(12) United States Patent
Roth et al.

(10) Patent No.: US 8,377,678 B2
(45) Date of Patent: Feb. 19, 2013

(54) METHODOLOGY FOR DETECTION, ENUMERATION, PROPAGATION AND MANIPULATION OF BACTERIOPHAGES

(75) Inventors: Jonathan Roth, Goshen, IN (US); James Larkin, Granger, IN (US); Fu-Chih Hsu, Granger, IN (US); Choi-Iok Rebecca Wong, Granger, IN (US); David A. Battigelli, Granger, IN (US); Geoffrey N. Roth, Goshen, IN (US)

(73) Assignee: Micrology Methods, LLC, Granger, IN (US)

( * ) Notice: Subject to any disclaimer, the term of this patent is extended or adjusted under 35 U.S.C. 154(b) by 501 days.

(21) Appl. No.: 12/309,670

(22) PCT Filed: Jul. 27, 2007

(86) PCT No.: PCT/US2007/017000
§ 371 (c)(1),
(2), (4) Date: Aug. 5, 2010

(87) PCT Pub. No.: WO2008/094202
PCT Pub. Date: Aug. 7, 2008

(65) Prior Publication Data
US 2010/0291539 A1    Nov. 18, 2010

Related U.S. Application Data

(60) Provisional application No. 60/833,738, filed on Jul. 27, 2006.

(51) Int. Cl.
*C12N 1/00* (2006.01)
*C12N 1/20* (2006.01)
*C12N 7/00* (2006.01)

(52) U.S. Cl. .................. 435/243; 435/5; 435/235.1

(58) Field of Classification Search .................. None
See application file for complete search history.

(56) References Cited

U.S. PATENT DOCUMENTS
6,090,541 A * 7/2000 Wicks et al. ............... 435/5

OTHER PUBLICATIONS
Fraser et al., Applied Microbiology, Feb. 1975, 29(2):305-306.*
Huang, et al. Nonuniform Spatial Patterns . . . ; Applied and Environmental Microbiology, Jun. 1995, p. 2252-2256.

* cited by examiner

*Primary Examiner* — Stacy B. Chen
(74) *Attorney, Agent, or Firm* — Botkin & Hall, LLP

(57) ABSTRACT

A method to propagate, enumerate and quantify bacteriophage(s) in a water sample or other aqueous sample was designed which contains ingredients to stimulate the growth of select bacterial species which are susceptible to infection by specific bacteriophage(s), in which interfering background organisms are either inhibited or inconsequential. Important features of the medium include oxidation-reduction compounds producing colored and/or fluorescent products, chromogenic and/or fluorogenic enzyme substrates, and temperature-independent gelling agent(s). A preferred combination is the growth medium containing 2,3,5-triphenyl tetrazolium chloride, 5-bromo-4-chloro-3-indolyl-B-D-galactoside, and appropriate gelling agents, which (when properly used) produces a dark red bacterial lawn containing teal blue-green, irregularly circular spots representing individual phage plaque, all discernible to the eye in visible light. The procedure can also be readily applied towards automatic counting systems under artificial illumination. The procedure can be employed with water samples and with elution buffers that can retain bacteriophages in suspension following contact by the buffer with foods, soils, hard surfaces and other solids that may be contaminated by bacteriophages.

7 Claims, No Drawings

METHODOLOGY FOR DETECTION, ENUMERATION, PROPAGATION AND MANIPULATION OF BACTERIOPHAGES

CROSS REFERENCE TO RELATED APPLICATION

This application claims the benefit of U.S. Provisional Application No. 60/833,738, filed Jul. 27, 2006 the disclosure of which is hereby incorporated by reference.

BACKGROUND OF THE INVENTION

Virtually all bacteria are host to viruses known as bacteriophages (hereinafter known as "phages"). These phages are species-specific, to the extent that a phage associated with the bacterium *Enterococcus faecalis* will be capable of infecting only *Enterococcus faecalis*, and a phage associated with *Escherichia coli* will infect only *Escherichia coli*. Viruses are non-cellular entities known as obligate parasites, which means they reproduce only within the cells of their specific hosts and they cannot replicate independently.

During lytic infection, phages will utilize the metabolic 'machinery' of the host and in the process multiply within the host cell to a point known as the "burst size", at which point the host cell ruptures and releases the newly formed phages into the environment. The host cell is killed in the process. The newly formed phage particles may persist in the environment where they are ready to infect additional suitable host cells that they encounter. Because certain phages are excreted or egested by warm-blooded animals including humans, their presence in the environment may be interpreted as an indication of fecal contamination.

Because phages and enteric viruses are generally considered more resistant than bacteria to antagonistic environmental factors, phages may exhibit longer survival times than the bacteria currently used to determine the extent of fecal contamination in the environment. If that is the case, then it follows that testing the environment (water, food, etc.) for the presence of phages may yield more useful correlative evidence of viral contamination than would be the case when bacterial indicators are used.

Unfortunately, until now no simple, accurate method of testing for phages as environmental indicators has been available. In food and water testing, one of the most important indicator bacteria is *Escherichia coli* and various phages specific to it have been well described and documented. Since *E. coli* is by definition a "coliform" bacterium, the phages associated with it are known as "coliphages". This bacterium and its viruses are well documented, the following discussion will be based on them. It should, however, be recognized that any microbial species and its phages might be used.

By minor changes in the nutrient formula and the use of different host bacteria, the methodology can be employed to detect any other bacteriophage specific to the host bacteria that can be propagated on a medium.

Currently, the approved methods for coliphage detection are detailed in *Standard Methods for the Examination of Water and Wastewater*, 20th edition as Method 9211 D., ISO Method 10705-2, ASTM Method 4201-96, and EPA Methods 1601/1602. These methods involve the use of agar based media which necessitates difficult and time-consuming temperature control procedures to maintain the integrity of samples and bacterial cultures. Because of the cumbersome, technique-specific nature of the Old Method(s), achievement of reproducible results is difficult for those laboratory technicians who lack experience with the methods or those who do not pay meticulous attention to detail, particularly as it relates to the temperature of the agar.

The approved enumerative methods are based upon the use of a semisolid matrix that functions to immobilize the host bacteria and the infecting phages. The medium must gel so that the bacteria grow within the gel-solid matrix, where they are attacked (infected) by phages present in the sample. When a bacterial host cell is infected with the virus, the virus reproduces within the host until the host cell is engorged with virus particles at which point it bursts and releases the viruses into the environment where they are free to infect new host cells. The consistency of the gel may affect the migration of phage particles in the medium. Those bacteria that are infected release many more phage particles which infect surrounding bacteria so that a clear zone of dead host cells appears in the "lawn" of dense living bacterial growth which covers most of the plate. This clear zone of necrosis is known as a viral "plaque" and the number of visible plaques is used to quantify the number of viruses originally present in the sample.

The use of coliphage qualitative and quantitative test methods are somewhat analogous to the testing for coliform bacteria in a given sample. Neither the coliphages nor the coliform bacteria are generally considered primary pathogens (disease-causing agents); rather, they are considered "indicators" of pathogenic contaminants that may be found in the same environment and their presence is generally assumed to indicate the potential presence of disease-causing microorganisms. Typical bacterial pathogens include species of genera such as *Salmonella* (typhoid and paratyphoid) or *Vibrio* (cholera). The absence of coliform bacteria is generally considered to reflect a likely absence of these and other bacterial pathogens because the indicator organisms are typically more numerous than pathogen bacteria in the environment and indicator and pathogenic bacteria generally exhibit similar survival times in the environment.

Because viral pathogens such as hepatitis A virus, the poliovirus group, noroviruses, and others tend to exhibit appreciable resilience in the environment and are characterized by extended survival times and in general to a high degree of resistance of antagonistic forces such as heat, freezing, and desiccation, for example, these viruses may be present even when the bacterial indicators are completely absent. Therefore, if a virus indicator such as a coliphage is used, there is an increased probability of capturing an actual virus contamination event when it occurs. Moreover, exclusive reliance upon bacterial indicators may result in the incorrect conclusion that pathogenic viruses are absent from the environmental sample.

SUMMARY OF THE INVENTION

Some of the basic materials suggested in the new invention are similar to those of the traditional agar based methods, but there are several very important and unique differences. Instead of the incorporation of agar into the media as the gelling agent, the gelling in this invention is accomplished by incorporating materials other than agar which convey very different properties and constraints to the method.

This invention has a purpose and is designed to produce a more accurate enumeration of the number of bacteriophages present in a sample by reducing the number of labile viruses inactivated by contact with materials at an elevated temperature.

DESCRIPTION OF THE INVENTION

The invention incorporates specific ingredient(s) that, when combined, result in the formation of a semi-solid or gelled matrix. The change in the physical state of these ingredients from a liquid to a semi-solid state is temperature-independent.

The ingredients consist of two types of materials, the first being one or more of a class of agents commonly referenced as "gums". These "gums" may include but not be limited to pectins, carrageenans, alginates, gellans, gelatins, xanthans, and guar. At least one of this ingredient type which has the property of combining with the second material type must be included in the invention composition. The second type of material consists of divalent metallic salts, with the preferred material being calcium chloride.

The combination of these two types of materials results in a gel which is an improved alternative to agar for the propagation of host bacteria and the detection and enumeration of bacteriophages that infect the host bacteria. One preferred choice of the invention incorporates pectin as the primary gelling agent, and the mechanism is similar to that of the Pectin Gel Method that is used and marketed by Micrology Laboratories of Goshen, Ind. and disclosed in U.S. Pat. No. 4,241,186, incorporated by reference herein.

The modification and application of Pectin Gel technology makes this invention novel and unique from the traditional agar based method, improving the ability to detect and enumerate bacteriophages that are present and viable in a sample, including those that are currently inactivated by the molten, hot (minimum 45° C.) agar medium.

Even small temperature increases well below the minimum 45° C. temperature of molten agar medium, such as seen when a human hosts spikes a fever to 39° C. is understood to inactivate viruses. However, the fact that some bacteriophages can be recovered and form plaques when a molten agar medium method is used may hide the non-obvious fact that other bacteriophages may have been present in the sample which are capable of infecting host bacteria but were not detected because they were inactivated by the heat and therefore cannot form plaques. These uncounted bacteriophages are not enumerated because they become damaged by the elevated temperature of the molten agar medium or because they attach to host bacteria that are damaged and inactivated by the elevated temperature of the molten agar medium.)

While the use of temperature independent gelling materials improves on the enumeration of bacteriophages by eliminating the temperature induced inactivation of labile viruses, this invention further incorporates other improvements over currently available, existing methods. For example:

1. The appearance of the plaque is generally apparent after 6 hrs. incubation time for coliform type bacteriophages.

2. The ease of seeing and counting the plaques present on the dish is greatly enhanced by the combination of a chromogenic substrate such as 5-Br-4-Cl-3-indolyl-â-Dgalactoside (X-Gal) and a bacterial stain such as 2, 3, 5 Triphenyl-2H-Tetrazolium Chloride (TCC). The mechanisms for these two compounds in the mix need to be explained and understood in order to comprehend the uniqueness of the method.

First, the presence of the X-Gal is important to the coloration of the plaque as the X-Gal is a chromogenic enzyme substrate which is cleaved by interaction with the enzyme galactosidase, resulting in an insoluble chemical dimer that assumes a teal blue-green color. Also a fluorogenic enzyme substrate such as 4-methylumbelliferyl-B-D-galactoside could be used as a color producing agent.

Therefore, when the bacteria (in the case of this example the bacteria are $E.\ coli$ or coliform introduced into the mix grow, they produce the enzyme galactosidase and the bacterial cells and aggregates of those cells assume the teal coloration. This coloration stays with the bacterial cells whether they are dead or alive. Therefore, without any other colorizing agent in the mix, the lawn of bacteria will turn a teal color, and even areas of plaque will be teal from the fact that the insoluble pigment was present before the bacteria were killed by the bacteriophage. The bacteriophage infects bacterial cells and replicates within the bacterial cells until the cells burst and release quantities of newly formed bacteriophage which can infect and kill other bacterial cells in the vicinity, thus forming a zone, or plaque, consisting of dead bacteria. This plaque forms an irregularly edged circular area which is what must be discerned and counted to determine the presence and quantity of bacteriophage in the original sample. Each circular plaque zone is considered the result of an original host bacterium being infected by a single bacteriophage. The use of the X-Gal alone may not result in easily seen plaques.

Therefore, an additional colorizer to increase and contrast the plaques from the rest of the bacterial lawn may be needed. This is where the TCC or some other similar oxidation reduction compound (Redox) becomes important. The TCC in the mix remains colorless in its oxidized state until the bacteria grow actively and cause it to be reduced, whereupon it becomes a red color. This reduction only occurs where there are living bacterial cells or aggregates and so the living portion of the bacterial lawn assumes a red color which is combined with the teal of the X-Gal and the red becomes dominant in the lighting conditions described.

The circular \plaque areas do contain only dead bacterial cells and therefore no reduction of the TCC occurs in the plaque and it stands out as a teal circular area in a deep red background lawn, so that it becomes very simple and easy to see and enumerate the Plaque. Therefore, the contrasting color that causes the circular Plaque to stand out will only occur if there is a colorizing agent activated by living cells. This explains one of the unique features of the method.

It should be understood that the X-Gal and TCC combination used in the example is not limiting.

One should be aware that there are many potential variations in the combinations of Redox reagents, antibiotics and chromogenic compounds that may be used successfully for this method. For example, there are various tetrazolium salts available which may give different colors when reduced, such as blue. The combination of a blue-producing T-salt with a pink or red chromogenic galactoside or glucuronide enzyme substrate would result in the phage plaque appearing pink or red with the background being blue or purple. Also redox reagents such as methylene blue or reazurin might be used. Regardless of the combinations chosen, the principles of the method are realized and achieved. Many variations of host bacteria, bacteriophages, temperature-independent gelling agents, chromogenic and fluorogenic substrates for various enzymes, and inhibitors of non-target bacteria can be described to produce an analogous testing capability, but the instructions for the general method are presented below.

3. Another advantage of the invention is that the likelihood of confusing small air bubbles in the medium with bacteriophage plaques is eliminated. When no chromogen is used in the medium (other methods) both the plaque and air bubbles appear as clear circular spots and are easily confused. With the new invention, air bubbles still appear as clear circular spots, but plaques appear as colored circular spots.

4. The size of the plaque areas produced by the new invention also are generally significantly larger and therefore more obvious and easily seen than those of other existing methodology. This is due to the unique properties of the gel that is produced by the pectin or other gum(s) used in the method versus the agar-based gel of other methods.

5. This invention also allows a large (up to 10 mL) sample to be tested in one standard sized petri dish. It is feasible that through the use of larger dishes, larger single samples could be run. Larger samples are advantageous when sample (test) materials contain very low numbers of bacteriophage. For example, if a water sample contains 20 bacteriophage/100 mL, a 1-4 mL sample will likely show as negative, while a 10 mL sample will contain 2 plaques.

6. The invention does not require the use of an overlay of the sample mix on the top of a prepoured plate or container. This makes the procedure much more energy and time effective.

7. The invention also takes advantage of antibiotics and antibiotic-resistant hosts for the suppression of interfering microorganisms that may obscure viral plaques. For example, conferring ampicillin, nalidixic acid and streptomycin resistance in the *E. coli* (or other bacterial type) strain used would eliminate most interference by extraneous organisms and eliminate the necessity of using other means of controlling that potential problem.

Example

Bacteriophage Quantitation from a Water Sample

The following are materials and formulations suggested for a generic set-up and procedure constituting the new invention. The final pH of the sterile Medium should be around 6.0-6.2 and may need to be adjusted with an appropriate solution such as 10% aqueous Potassium Carbonate. The need for this depends on whether the only gelling agent in the Nutrient Medium is the Low Methoxyl Pectin or if a mix of pectin with other gums such as alginate, carageenan, etc. are used.

Reagents and Supplies Needed:
1. A sterile Nutrient Medium with the following formulation is provided in a container.
FORMULATION (ingredients for one Liter):

| | |
|---|---|
| Proteose Peptone #3 | 30 gm. |
| Soy Peptone | 10 gm. |
| Potassium Phosphate (dibasic) | 4 gm. |
| Sodium Chloride | 6 gm. |
| Low Methoxyl Pectin | 25 gm. |
| X-Gal (5Br4Cl3IndolylBDgalactoside) | 180 mg. |
| IPTG (IsopropylBDthiogalactoside) | 180 mg. |

2. Tryptic Soy Broth (TSB) such as manufactured by Difco or BBL
3. Sterile reagent water
4. Bacterial Stain (sterile 5% 2,3,5 Triphenyl-2H-Tetrazolium Chloride, abbreviated TCC)
5. Bacterial Host Cells specific for Bacteriophage
6. Specific Bacteriophage for use as positive control.
7. Sterile Pretreated Petri Dishes containing semi-dry layer holding 225 mg of Calcium Chloride Procedure:
1. All materials and solutions are equalized to room temperature (22-35 C.—exact temp. not crucial)
2. To a bottle containing 10 mL of sterile Nutrient Medium, add test water sample or test sample concentrate or instead, to create a control, add a solution containing a known concentration of Specific Bacteriophage. If needed add TSB or sterile reagent water to bring total volume to 18-20 mL. Also, then add 70 uL of Bacterial Stain, and 0.3 mL log phase Bacterial Host Cells.

3. Mix the combined solution by swirling several times (do not vortex to avoid creating excessive bubbles) and pour the entire mixture into a sterile Pretreated Petri Dish.

TABLE 1

Various combinations of sample and TSB or sterile reagent water volumes capable of producing acceptable plaque formation.
Various combinations of sample and TSB or sterile reagent water volumes capable of producing acceptable plaque formation.

| Sample Volume (mL) | Sterile TSB or Sterile water (mL) | Nutrient Medium (mL) | Bacterial Stain (uL) | Bacterial Host (mL) |
|---|---|---|---|---|
| 1 | 7 | 10 | 70 | 0.3 |
| 2 | 6 | 10 | 70 | 0.3 |
| 3 | 5 | 10 | 70 | 0.3 |
| 4 | 4 | 10 | 70 | 0.3 |
| 5 | 3 | 10 | 70 | 0.3 |
| 6 | 2 | 10 | 70 | 0.3 |
| 7 | 1 | 10 | 70 | 0.3 |

3. Swirl the dish gently several times and place the dish (upright) on a level shelf of an incubator. If the test is for coliform bacterial types, the incubator should be set at 35° C. The mixture in the dish will gel within 1 hour. Incubate the dishes for 12-16 hours.

4. Remove the dish from the incubator and count the circular teal plaques on the red bacterial lawn. Examination of the dish for the plaques is best done with the dish placed on a light box or colony counter and a light source from the top of the dish may also be helpful. The plaque color will be more intense when the light shines from the top of the dish.

The invention herein described eliminates the difficulties of previously described approachs and offers an effective and easy way to accomplish the stated goals, not only saving time and energy, but increasing the accuracy and recovery of the target phages.

The described example for the new invention allows the rapid assessment of coliphages in/on virtually any substrate including water, food and environmental surfaces. It therefore has great utility for the testing of water, food and other materials where convenient, accurate and precise coliphage results are useful. The invention is simple to use, and results are precise and reproducible. It requires minimal equipment and technician time to obtain accurate and useful information with minimal chance of error. The components are inexpensive and it requires little time and energy to operate.

What is claimed is:

1. A growth test medium for the detection of the presence of bacterial viruses in a sample containing bacteria, the test medium comprising:
   a nutrient growth medium;
   a gum capable of forming a solid when combined with an additional compound, the forming of the solid is temperature-independent, wherein said additional compound is a divalent metal;
   a first compound that when cleaved by enzymatic reaction with said bacteria is capable of causing the bacteria to assume a first color and the first color is retained with cellular material of said bacteria after the bacteria are killed by a virus, wherein said first compound is a chromogenic or a fluorogenic enzyme substrate; and
   a second compound that undergoes chemical reduction when proximate or in contact with living bacteria to form a second color so that areas containing living bacteria assume a third color defined by a combination of the first and second colors, and said areas containing living bacteria are visually distinguishable from areas of non-living bacteria, which are colored only by the first compound, wherein the second compound is a tetrazolium.

2. The test medium of claim 1, wherein the divalent metal is calcium.

3. The test medium of claim 1, wherein the chromogenic enzyme substrate is 5-bromo-4-chloro-3-indolyl-B-D-glucuronide and said fluorogenic enzyme substrate is 4-methylumbelliferyl-B-D-glucuronide.

4. The test medium of claim 1, wherein said chromogenic enzyme substrate is 5-bromo-4-chloro-3-indolyl-B-D-galactoside and said fluorogenic enzyme substrate is 4-methylumbelliferyl-B-D-galactoside.

5. The test medium of claim 1, wherein the gum is a mixture that includes at least one constituent selected from the group consisting of a pectin, carrageenan, alginate, gellan, gelatin, xanthan or guar, said mixture is combinable with the divalent metal.

6. The test medium of claim 1, wherein the tetrazolium is 2,3,5 triphenyl tetrazolium chloride.

7. A method for testing the presence of and quantitatively identifying and differentiating bacterial viruses in a test sample comprising the steps of:

inoculating a growth test medium capable of forming a solid with said test sample and a specific bacterial culture, said test medium includes at least one chromogenic or one fluorogenic enzyme substrate capable of producing a first color or fluorescence when cleaved by enzymatic reaction with the specific bacterial culture, wherein the chromogenic enzyme substrate is 5-bromo-4-chloro-3-indolyl-B-D-glucuronide and said fluorogenic enzyme substrate is 4-methylumbelliferyl-B-D-glucuronide, at least one oxidation-reduction compound capable of producing a second color or fluorescence, the oxidation-reduction compound is reduced in the presence of a living bacteria of the specific bacterial culture, the second color or fluorescence is a product of the reduction of the oxidation-reduction compound, wherein the oxidation-reduction compound is 2,3,5 triphenyl tetrazolium chloride, said colored or fluorescent products being discernible in visible or ultraviolet light;

introducing the test medium containing said test sample, bacterial culture, oxidation-reduction compound and one chromogenic or fluorogenic substrate into an environment containing divalent metallic ions which induce solidification of the mixture independent of ambient temperature, wherein said divalent metallic ions are calcium ions; and incubating said test medium solidified mixture to produce growth of said specific bacterial species in a dense lawn of bacteria colored by a combination of both first and second colors or fluorescence, wherein the presence of both said first and said second colors indicates the presence of said bacterial virus.

* * * * *